US 6,230,053 B1

(12) United States Patent
Magin

(10) Patent No.: US 6,230,053 B1
(45) Date of Patent: May 8, 2001

(54) DEFIBRILLATOR HAVING A MONITOR WITH ROTATABLE SCREEN CONTENT

(75) Inventor: Thomas Magin, Umkirch (DE)

(73) Assignee: Marquette Hellige GmbH, Freiburg (DE)

(*) Notice: Subject to any disclaimer, the term of this patent is extended or adjusted under 35 U.S.C. 154(b) by 0 days.

(21) Appl. No.: 09/243,727

(22) Filed: Feb. 3, 1999

Related U.S. Application Data

(63) Continuation-in-part of application No. 09/185,454, filed on Nov. 3, 1998.

(30) Foreign Application Priority Data

Nov. 14, 1997 (DE) .............................. 197 50 632

(51) Int. Cl.$^7$ .................................................. A61N 1/39
(52) U.S. Cl. .................................................. 607/5
(58) Field of Search ....................................... 607/5

(56) References Cited

U.S. PATENT DOCUMENTS

| 4,187,858 | 2/1980 | Day et al. . |
| 4,590,943 | 5/1986 | Paull et al. . |
| 5,566,098 | 10/1996 | Lucente et al. .................. 364/708.1 |

FOREIGN PATENT DOCUMENTS

| 0167122 | 1/1986 | (EP) . |
| 0431581 | 6/1991 | (EP) .............................. G09G/1/00 |
| 0609500 | 8/1994 | (EP) . |
| 0757912 | 2/1997 | (EP) .............................. A61N/1/39 |
| 2301201A | 11/1996 | (GB) . |

OTHER PUBLICATIONS

Product Brochure for CardioServ Version 4, Marquette Hellige Medical Systems, pp. 53 and 91.
Bruker Product Brochure for Defigard 1001 and 1002.
Bruker Product Brochure for Defigard 2002.
Product Brochure for CardioServ Version 3, Marquette Hellige Medical Systems, p. 6–6.

Primary Examiner—Carl H. Layno
(74) Attorney, Agent, or Firm—Michael Best & Friedrich LLP; Christian G. Cabou

(57) ABSTRACT

A defibrillator (1) having an integrated surveillance monitor (10), on the screen of which vital parameters of a patient can be displayed in the form of a rotatable screen content, having a built-in accumulator (9) for power supply independently of the main power supply and having a connection device (2, 3, 7) for external power supply and for recharging the accumulator (9). The screen content is rotatable from a first position relative to the housing to a second position relative to the housing in response to a change in position of the housing.

38 Claims, 1 Drawing Sheet

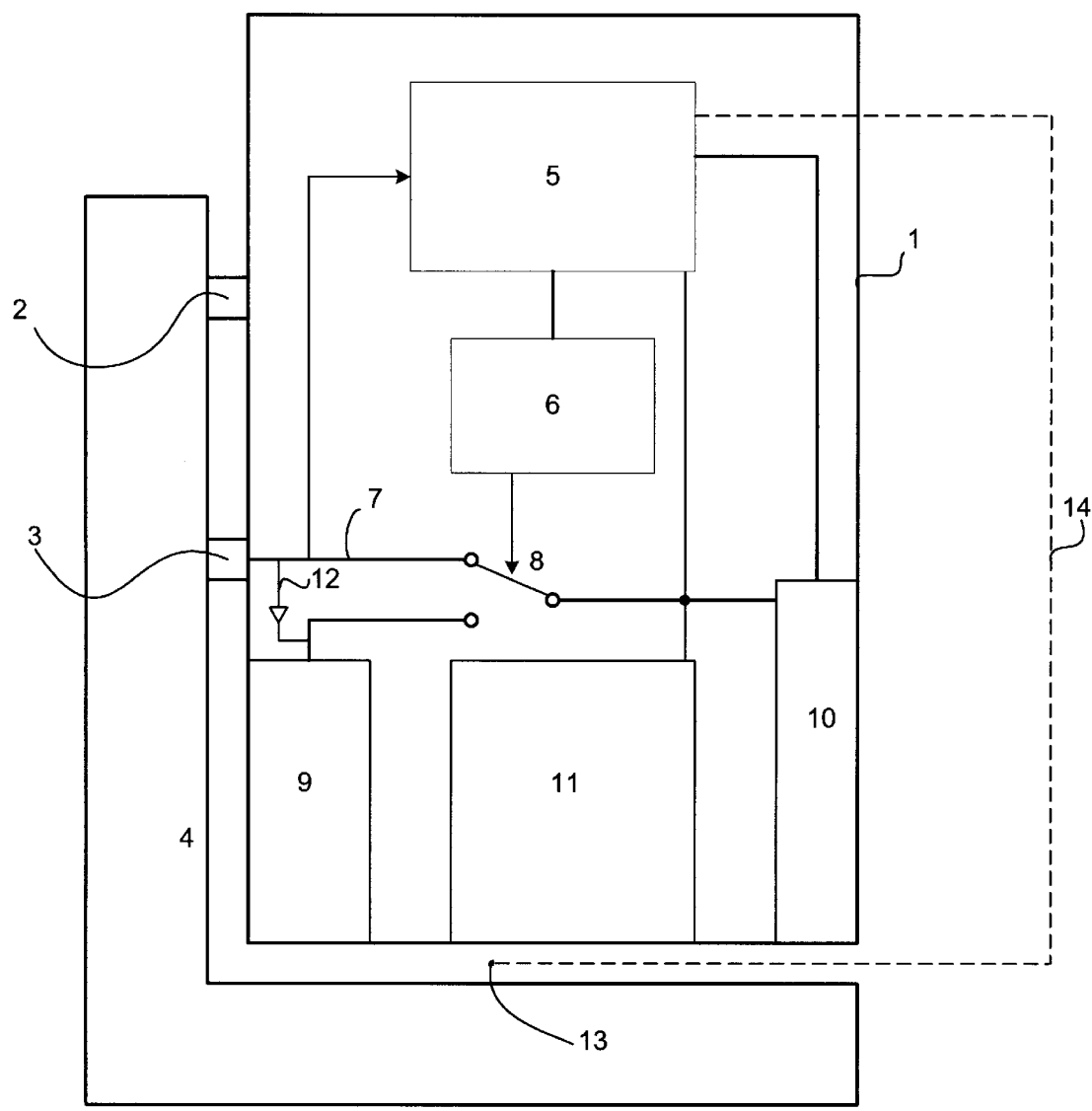

DEFIBRILLATOR HAVING A MONITOR WITH ROTATABLE SCREEN CONTENT

RELATED APPLICATIONS

This application is a continuation-in-part of co-pending U.S. application Ser. No. 09/185,454 filed Nov. 3, 1998, which claims the benefit under 35 U.S.C. §119 of German Application No. 197 50 632.1, filed Nov. 14, 1997.

BACKGROUND OF THE INVENTION

The present invention relates to a defibrillator having an integrated surveillance monitor, on the screen of which vital parameters of a patient can be displayed in the form of a rotatable screen content, having a built in power supply device for power supply independent of the main power supply and having a connection device for the external power supply of the defibrillator.

Defibrillators for external or transthoracic defibrillation form part of the equipment of rescue facilities, such as in particular rescue vehicles, and are thus used in differing practical situations, namely on the one hand directly at the place of application outside the rescue facility and on the other hand during transport of the patient using the rescue facility. That is to say that the defibrillator is removed from the rescue facility upon arrival of the rescue facility at the place of application, in order to be utilized for the treatment of the patient, who is usually lying on the ground. During transport of the patient to the hospital using the rescue facility, the defibrillator is likewise needed; however, for this purpose it is inserted into a special mounting within the rescue facility.

When used outside the rescue facility the defibrillator is powered by means of its own power supply, i.e. preferably an accumulator, while the defibrillator inserted in its mounting within the rescue facility draws its energy from the on-board power supply of the rescue facility; in this case, the accumulator of the defibrillator is at the same time recharged from the on-board power supply.

A defibrillator has a substantially parallelepipedic housing, which, in the course of treatment of a patient outside the rescue facility, rests flat on the ground. Within the rescue facility for reasons of space the defibrillator is inserted "edgewise" into its mounting.

This differing arrangement of the defibrillator in the case of use outside the rescue facility and in the case of use within the rescue facility now gives rise to a shortcoming, and the most widely varying efforts have already been made to eliminate this shortcoming.

As is known, a defibrillator does indeed have a surveillance monitor, on which the vital parameters of a patient are displayed. These vital parameters include at least an electrocardiogram (ECG) and, where appropriate, further quantities in addition. Accordingly, the surveillance monitor provides the physician or paramedic with a report on the success or lack of success of the use of the defibrillator on the patient. Thus, constant observation by the physician or paramedic is of great importance.

As has, however, already been explained hereinabove, the defibrillator is situated in different positions when used outside the rescue facility and when used within the rescue facility; this necessarily also involves different positions of the surveillance monitor, and thus of the screen thereof.

This means that an image which appears in "normal" form on the screen when the defibrillator is used outside the rescue facility may appear in a "vertically inverted" form in the case of use within the rescue facility when the defibrillator is situated in a mounting, since, as a consequence of the different positioning of the defibrillator, the screen has been rotated through 180°. It does not need to be emphasized that the viewing and evaluation of a "vertically inverted" image is extremely laborious for the physician or paramedic.

To overcome this problem, a defibrillator has already been developed, the screen content of which can be rotated by means of the actuation of an operating element. Thus, in addition to the operating elements which are needed for medical reasons, such defibrillators also have a further operating element which has to be actuated and set separately after the defibrillator has been inserted into the mounting within the rescue facility, in order to obtain the signal display on the screen of the surveillance monitor in the accustomed fashion, i.e. "not vertically inverted".

However, precisely when a patient is brought into a rescue facility, the most widely varying necessary actions have to be performed by the physician or paramedic, so that the setting of a separate operating element on the defibrillator to rotate the screen content thereof is perceived as troublesome.

SUMMARY OF THE INVENTION

Accordingly, it is the object of the present invention to provide a defibrillator having a surveillance monitor with a rotatable screen content, in the case of which a physician or paramedic obtains the display of the screen content in the correct arrangement and not "vertically inverted" on the surveillance monitor of the defibrillator, without additional manipulations or settings, irrespective of the place of application of the defibrillator outside or within a rescue facility.

In the case of a defibrillator of the initially mentioned type, this object is achieved according to the invention in that the screen content is automatically rotatable in dependence on the application of the external power supply, or in dependence on the insertion of the defibrillator into a mounting, respectively.

Thus, the invention follows a surprisingly simple path: by means of a sensor, it is discerned whether the power supply of the defibrillator is being effected via the on-board power supply of the rescue facility, or whether the defibrillator is inserted into a mounting. If it is found, for example, that the power supply is being undertaken via the on-board power supply of the rescue facility, then the screen content displayed on the surveillance monitor of the defibrillator is rotated through 180°, and vice versa. It is thus achieved that, after insertion of the defibrillator in its mounting within the rescue facility and after the establishment of contact of contact springs of the defibrillator with the on-board power supply of the rescue facility, or after the establishment of contact of a sensor, respectively, the screen content is immediately rotated without manual intervention by the physician or paramedic, so that it can again be viewed in the normal position and not "vertically inverted". In this case no additional manipulations or settings are necessary, so that it is also the case that, for this purpose, the treatment of the patient does not need to be interrupted.

In this way, the invention permits a special advantage, namely an "automatic" rotation of the screen content on the surveillance monitor, in dependence on the place of application of the defibrillator; this was not possible previously, with the prior art.

As the defibrillator's power supply device independent of the on-board power supply use is preferably made of an accumulator which, upon application of the external power supply, can automatically be recharged from the on-board power supply of the rescue facility.

In a development of the invention, it is provided that the rotatability of the screen content can be activated in dependence on the power supply or in dependence on the insertion into a mounting, respectively, prior to the first inception of operation of the defibrillator. That is to say that it is possible that the rotatability of the screen content is not activated. This may be expedient in special cases, in which, on an exceptional basis, the defibrillator is accommodated within the rescue facility in such a way that its surveillance monitor is in the same position as outside the rescue facility. In this case, a rotatability of the screen content is undesired, so that the activation of the rotatability is expediently not undertaken.

In this connection, it should be mentioned that rescue facilities are to be understood in general as referring to motor vehicles, rail vehicles, airplanes, helicopters and watercraft, although, of course, motor vehicles represent the preferred area of application. Where sufficient space is available, the defibrillator is not necessarily inserted "edgewise" in a mounting within the rescue facility; this means that, as has been explained hereinabove, the surveillance monitor reproduces its screen content in the normal position.

Another development of the present invention resides in that the screen content can additionally be rotated by means of a manually actuated switch. On this basis, it is achieved that in exceptional cases the rotation of the screen content can be undertaken manually, i.e. as in the case of the above mentioned, already existing systems; this is advisable, for example, in circumstances in which the defibrillator cannot be powered, in the rescue facility, from the on-board power supply of the latter, because, for example, that power supply has interruptions to the contact springs.

Finally, another development of the invention resides in a micro-controller, connected downstream of the connection devices, for the surveillance of the voltage present at the connection devices. Such a micro-controller is particularly advantageous for the detection of the voltage delivered by the on-board power supply of the rescue facility.

DESCRIPTION OF THE DRAWING

In the text which follows, the invention is explained in greater detail with reference to the single drawing in which a block diagram of the defibrillator according to the invention is diagrammatically represented.

DESCRIPTION OF THE PREFERRED EMBODIMENT

The figure shows a defibrillator 1, which is attached by means of contact springs 2, 3 to a mounting 4 of a rescue facility which is not shown. Earth potential is for example supplied via the contact spring 2, while the on-board power supply having the supply voltage of 12 V, for example, is applied to the contact spring 3.

In the defibrillator 1 there are a main microprocessor 5 for controlling the defibrillator in its entirety, and a micro-controller 6 which scans an input line 7 connected to the contact spring 3 in the case of insertion into the mounting 4 and controls a switch 8 in dependence on the detected voltage. This switch 8 is connected either to the input line 7 for supply via the on-board power supply or to an accumulator 9. In place of the accumulator, it is also possible to use, for example, a battery.

It should be noted that this accumulator 9 is recharged when the defibrillator 1 is connected to the on-board power supply) this is diagrammatically indicated in the figure by a corresponding line 12 with diode.

In addition, the defibrillator 1 includes a surveillance monitor 10 having a screen, for example a liquid crystal display, as well as a high voltage section 11. The high voltage section 11 delivers (controlled by the main microprocessor 5) current pulses having a time duration of approximately 4–8 ms for electrodes of the size of the palm of the hand which are to be applied to the chest wall of the patient (not shown). As has already been explained hereinabove, the vital parameters of the patient are displayed on the screen of the surveillance monitor 10.

When the defibrillator 1 has been taken out of the mounting 4, the micro-controller 6 then detects that a power supply via the input line 7 is no longer present. It then switches over the switch 8 to the accumulator 9, so that the latter powers the main microprocessor 5, the surveillance monitor 10 and the high voltage section 11.

When the defibrillator 1 has been taken out of the mounting 4, it is then laid flat on the ground, in order to be in a stable position for a treatment of a patient. In this position, the surveillance monitor 10 displays the screen content in the correct position for a physician or paramedic on its screen.

When, following a first emergency treatment, the patient is then brought together with the defibrillator into the rescue facility and the defibrillator is inserted into the mounting 4, the screen content then appears on the surveillance monitor 10 in a form which is per se "vertically inverted". Since, however, the micro-controller 6 immediately detects that, following contacting via the contact springs 2, 3, the power supply is being effected from the on-board power supply of the rescue facility, since the on input line 7, it immediately switches over the switch 8 to the on-board power supply, so that the latter now powers the defibrillator 1. Simultaneously with this switching over, a rotation of the screen content on the screen of the surveillance monitor 10 through 180° is effected by means of the microprocessor 5, so that the screen content can now be normally read, within the rescue facility as well, from the point of view of the physician or paramedic.

The defibrillator 1 is designed in such a way that the rotatability of the screen content can be activated via the main microprocessor 5 in dependence on the power supply via input line 7 or the on-board power supply, or in dependence on the insertion of the defibrillator into a mounting, prior to the first inception of operation of the defibrillator 1. Practical applications are indeed feasible in which such an activation is not desired, when for example the defibrillator is likewise anchored in a "flat position" within the rescue facility. Accordingly, the rotatability of the screen content does not necessarily need to be activated.

Moreover, it is also possible to provide an additional manual switch (likewise not shown) by means of which the rotation of the screen content can be undertaken manually, independently of the power supply.

In the case of the above illustrative embodiment, the screen content is automatically rotated in dependence upon the application of the external power supply (on-board power supply). This external power supply is applied when the defibrillator 1 is inserted into the mounting 4. Accordingly, in general, in place of the application of the external power supply it is also possible to detect the insertion of the defibrillator 1 into the mounting 4, in order to undertake the rotation of the screen content automatically in dependence thereon.

The insertion of the defibrillator 1 into the mounting 4 can be detected by means of a magnetically or optically or mechanically or electrically controlled element 13, which is activated when the defibrillator 1 passes into the mounting 4. This insertion of the defibrillator 1 into the mounting 4 is reported to the microprocessor 5 (cf. broken line 14), which then undertakes the rotation of the screen content on the surveillance monitor 10. Examples of the element 13 are a switching device based on induction or a magnetic field, such as for example an inductive proximity switch or a reed relay, a simple mechanical switch, an optical switching element, such as for example a hybrid light barrier or a pyroelectric sensor, a capacitive switch or acoustic sensors of any type.

What is claimed is:

1. A defibrillator having an integrated surveillance monitor (10), on the screen of which vital parameters of a patient can be displayed in the form of a rotatable screen content, having a built-in power supply device (9) for supplying power independently of an external power supply and having a connection device (2, 3, 7) for connecting the external power supply to the defibrillator, characterized in that the screen content is automatically rotatable in dependence on the insertion of the defibrillator into a mounting.

2. A defibrillator according to claim 1, characterized in that the built-in power supply device (9) is an accumulator which is rechargeable upon application of the external power supply.

3. A defibrillator according to claim 1, characterized in that the automatic rotatability of the screen content can be activated in dependence on the application of the external power supply prior to the first inception of operation of the defibrillator (1).

4. A defibrillator according to claim 1, characterized in that the screen content can be rotated by means of a manually actuated device.

5. A defibrillator according to claim 1, characterized by a micro-controller (6), connected downstream of the connection device (2, 3, 7), for the surveillance of the voltage present at the connection device (2, 3, 7).

6. A defibrillator according to claim 1, characterized in that the insertion of the defibrillator (1) in the mounting can be detected by means of a mechanical or magnetic or optical or electrical switch.

7. A defibrillator adapted for convertible use between an ambulance wherein the defibrillator is mounted in a mount within the ambulance, and portable use external to the ambulance, the defibrillator comprising:

a housing of a size adapted to fit within the mount in the ambulance;

a display monitor for displaying vital parameters of a patient connected to the defibrillator; and a controller for displaying the vital parameters in a first position relative to the housing when the housing is out of the mount, and for displaying the vital parameters of the patient in a second position relative to the housing when the housing is positioned in the mount.

8. A defibrillator as set forth in claim 7 wherein the ambulance further includes a power supply connected to the mount, and wherein the controller automatically changes the screen content between the first position and the second position when the power supply within the mount is connected to the defibrillator.

9. A defibrillator as set forth in claim 7, and further comprising a rechargeable battery mounted in the housing.

10. A defibrillator as set forth in claim 7, and further comprising a switch actuated when the defibrillator is positioned in the mount to change the screen content from the first position to the second position.

11. A defibrillator as set forth in claim 10, wherein the switch is a mechanical switch.

12. A defibrillator as set forth in claim 10, wherein the switch is a reed relay.

13. A defibrillator as set forth in claim 10, wherein the switch is an inductive proximity switch.

14. A defibrillator as set forth in claim 10, wherein the switch is an optical switching element.

15. A method of displaying information on a portable defibrillator convertible for use in combination with an ambulance having a mounting apparatus for supporting the portable defibrillator, or for use as a portable defibrillator external to the ambulance, the defibrillator having a housing adapted to fit within the mounting apparatus, and a display monitor supported in the housing, said method comprising:

displaying the information on the display monitor in a first position relative to the housing when the defibrillator is outside of the mounting apparatus;

inserting the defibrillator into the mounting apparatus; and automatically changing the position of the information on the display monitor to a second position relative to the housing when the defibrillator is inserted into the mounting apparatus.

16. A method as set forth in claim 15 wherein the act of automatically changing the position of the information on the display monitor includes actuating a switching device automatically when the defibrillator is inserted into the mounting apparatus.

17. A method as set forth in claim 15 wherein the act of automatically changing the position of the information on the display monitor includes detecting the act of inserting the defibrillator into the mounting apparatus using a magnetically controlled element.

18. A method as set forth in claim 15 wherein the act of automatically changing the position of the information on the display monitor includes detecting the act of inserting the defibrillator into the mounting apparatus using an optically controlled element.

19. A method as set forth in claim 15 wherein the act of automatically changing the position of the information on the display monitor includes detecting the act of inserting the defibrillator into the mounting apparatus using a mechanically controlled element.

20. A method as set forth in claim 15 wherein the act of automatically changing the position of the information on the display monitor includes detecting the act of inserting the defibrillator into the mounting apparatus using an electrically controlled element.

21. A defibrillator, comprising:

a housing;

a display monitor supported in the housing and displaying vital parameters of a patient connected to the defibrillator; and a controller generating the vital parameters on the display monitor in a first position relative to the housing, and automatically generating the vital parameters on the display monitor in a second position relative to the housing in response to a change in position of the housing.

22. A defibrillator as set forth in claim 21, wherein the housing is adapted for a mount, and wherein the controller automatically generates the vital parameters on the display monitor in the second position when the housing is within the mount.

23. A defibrillator as set forth in claim 22, and further comprising an input disposed in the housing, connected to the controller, and adapted to receive an external power source, wherein the input receives power from the external power source when the defibrillator is positioned within the mount, and wherein the controller generates the vital parameters in the second orientation in response to receiving power from the input.

24. A defibrillator as set forth in claim 21, and further comprising a rechargeable battery mounted in the housing.

25. A defibrillator as set forth in claim 21, and further comprising a switch actuated in response to the change in position of the housing.

26. A defibrillator as set forth in claim 25, wherein the defibrillator is adapted for a mount, and wherein the switch is actuated when the defibrillator is position in the mount.

27. A defibrillator as set forth in claim 25, wherein the switch is a mechanical switch.

28. A defibrillator as set forth in claim 25, wherein the switch is a reed relay.

29. A defibrillator as set forth in claim 25, wherein the switch is an inductive proximity switch.

30. A defibrillator as set forth in claim 25, wherein the switch is an optical switching element.

31. A method of displaying information on a portable defibrillator having a housing and a display monitor supported in the housing, said method comprising the acts of:
   displaying the information on the display monitor in a first position relative to the housing; and
   automatically changing the position of the information on the display monitor to a second position relative to the housing in response to a change in position of the housing.

32. A method as set forth in claim 31, wherein the defibrillator is adapted for use with a mounting apparatus for supporting the defibrillator, and the method further comprises the act of inserting the defibrillator into the mounting apparatus prior to the act of automatically changing the position of the information on the display monitor.

33. A method as set forth in claim 31, wherein the act of automatically changing the position of the information on the display monitor includes the act of actuating a switching device.

34. A method as set forth in claim 33, wherein the defibrillator is adapted for use with a mounting apparatus for supporting the defibrillator, and wherein the act of actuating a switching device is automatic when the defibrillator is inserted into the mounting apparatus.

35. A method as set forth in claim 33, wherein the act of automatically changing the position of the information on the display monitor includes the act of detecting the act of actuating a switching device using a magnetically controlled element.

36. A method as set forth in claim 33, wherein the act of automatically changing the position of the information on the display monitor includes the act of detecting the act of actuating a switching device using an optically controlled element.

37. A method as set forth in claim 33, wherein the act of automatically changing the position of the information on the display monitor includes the act of detecting the act of actuating a switching device using a mechanically controlled element.

38. A method as set forth in claim 33, wherein the act of automatically changing the position of the information on the display monitor includes the act of detecting the act of actuating a switching device using an electrically controlled element.

\* \* \* \* \*